United States Patent [19]

Waller et al.

[11] Patent Number: 5,298,650

[45] Date of Patent: Mar. 29, 1994

[54] PROCESS FOR PRODUCING ORGANIC ESTERS BY REACTING A CARBOXYLIC ACID AND A DIALKYL ETHER

[75] Inventors: Francis J. Waller; William F. Burgoyne, Jr., both of Allentown, Pa.

[73] Assignee: Air Products and Chemicals, Inc., Allentown, Pa.

[21] Appl. No.: 868,914

[22] Filed: Apr. 15, 1992

[51] Int. Cl.$^5$ ............................................. C07C 67/24
[52] U.S. Cl. ........................... 560/240; 554/162; 562/103; 562/105; 562/112
[58] Field of Search ............ 560/240, 105, 112, 103; 554/162

[56] References Cited

U.S. PATENT DOCUMENTS

| | | | |
|---|---|---|---|
| 2,629,735 | 2/1953 | Cottle | 560/240 |
| 3,510,511 | 5/1970 | Conseiller et al. | 260/496 |
| 4,590,294 | 5/1986 | Ballantine | 560/240 |

OTHER PUBLICATIONS

Derevitskaya & Coworkers, Tetrahedron Letters, 49 (1970) 4269.

*Primary Examiner*—Michael L. Shippen
*Attorney, Agent, or Firm*—Keith D. Gourley; James C. Simmons; William F. Marsh

[57] ABSTRACT

The present invention is a process for producing organic esters wherein a dialkyl ether and a carboxylic acid are reacted in the presence of a solid phase acidic catalyst having an acidity factor of at least 0.30, preferably at least 1, under reaction conditions sufficient to form a reaction mixture comprising the desired organic ester and an alcohol and recovering the organic ester. For example, methyl acetate can be prepared by reacting dimethyl ether and acetic acid in the presence of montmorillonite, amorphous silica-alumina or κ-alumina under conditions sufficient to form methyl acetate. While typical processes produce an azeotropic mixture of the desired organic ester and water, the claimed process utilizes a combination or reactants and catalysts wherein water is not produced in appreciable amounts. Therefore, the organic ester product can be separated conveniently thereby avoiding a cumbersome azeotropic distillation step as required in prior art processes.

12 Claims, No Drawings

PROCESS FOR PRODUCING ORGANIC ESTERS BY REACTING A CARBOXYLIC ACID AND A DIALKYL ETHER

TECHNICAL FIELD OF THE INVENTION

The present invention is a process for producing organic esters wherein a dialkyl ether and a carboxylic acid are reacted in the presence of a catalytic amount of a solid phase acidic catalyst having an acidity factor of at least 0.30, preferably at least 1, under reaction conditions sufficient to form the desired organic ester. Organic esters are used in numerous applications such as solvents in coating compositions and as plasticizers.

BACKGROUND OF THE INVENTION

Organic esters, represented by the generic formula, $RCO_2R'$ wherein R and R' are independently selected from an organic functionality, are utilized in numerous applications. Recent data indicate that more than 600 esters are currently sold in the United States and more than 100 esters are available in medium and bulk lots. On the basis of bulk production, poly(ethylene rerephthalate) is prepared in greatest quantity and is used in manufacturing polyester fibers and thermosetting fibers. Poly(ethylene terephthalate) is typically prepared by reacting terephthalic acid and ethylene glycol or by transesterification of dimethyl terephthalate with ethylene glycol.

Numerous catalytic processes are known for producing organic esters including reacting an alcohol and either an acid anhydride, an acid chloride, an amide or a nitrile in the presence of a suitable catalyst under reaction conditions sufficient to form the desired product. For example, organic esters can be prepared by reacting a carboxylic acid and an alcohol in the presence of catalysts such as strong mineral acids, tin salts, organs-titanates, silica gel and cation-exchange resins. Unfortunately, these reactions proceed via a reversible equilibrium and can be driven toward completion only by removing the desired ester product or water.

Highly volatile organic esters such as methyl formate, methyl acetate and ethyl formate, typically have lower boiling points than their corresponding alcohols and can be readily removed from the product mixture by conventional methods. However, water cannot be easily separated by simple distillation from aliphatic alcohols and esters of medium volatility because the product mixture forms an azeotrope. Consequently, processes for making such esters are highly energy intensive because the water/ester azeotrope must be broken in order to recover the desired ester.

U.S. Pat. No. 3,510,511 discloses a process for preparing an ester by reacting a carboxylic acid and an alkyl ether. The process comprises continuously introducing an ether of an alkanol and a carboxylic acid simultaneously in a proportion, two moles acid to one mole ether, into a boiling mixture initially consisting of sulfuric acid and the ether in a proportion of 0.7 to 1.3 mol of sulfuric acid per mol of ether; continuously extracting the vapors evolved from the reaction mixture and isolating the ether product from water via fractional distillation.

Derevitskaya and coworkers, Tetrahedron Letters, 49 (1970) 4269 disclose a process for preparing alkyl esters by reacting an alkyl tert-butyl ether and a carboxylic acid in the presence of a catalytic amount of a proton-donating agent such as sulfuric acid or para-toluenesulfonic acid. The reaction is represented by the formula:

$$R\text{—}O\text{-tert-}C_4H_9 + R'\text{—}CO_2H \rightarrow R'\text{—}CO_2R + CH_2\text{=}C(CH_3)_2 + H_2O$$

The driving force of the above-mentioned reaction results from evolution of isobutylene. The desired organic ester is separated from the reaction mixture by diluting the mixture with diethyl ether, washing with aqueous sodium hydrogen carbonate and water and drying over sodium sulfate or magnesium sulfate. Following removal of diethyl ether, the residue is distilled to yield the desired ester.

Considerable research is being conducted in order to develop a process for preparing organic esters which eliminates the shortcomings of the above-mentioned prior art processes. Those skilled in the art of producing organic esters are particularly interested in commercial processes wherein water is not produced in appreciable quantities.

BRIEF SUMMARY OF THE INVENTION

The present invention is a process for producing organic esters which comprises reacting a carboxylic acid and a dialkyl ether in the presence of a catalytic amount of a solid phase acid catalyst having an acidity factor of at least 0.30, preferably at least 1, under conditions sufficient to form the organic ester and recovering the organic ester. The instant process utilizes a new class of catalysts which is capable of producing a product mixture which is substantially free of water thereby overcoming numerous problems associated with prior art processes wherein the desired organic ester must be separated from the unwanted water via fractional distillation.

The catalysts according to the present process consist essentially of a solid phase acidic catalyst having an acidity factor of at least 0.30, preferably at least 1. Suitable solid phase acidic catalysts include Lewis acids such as gamma-alumina and κ-alumina. Solid phase Bronsted acids having an acidity factor of at least 0.30 include naturally occurring and synthetically prepared zeolites, amorphous silica-alumina, cogels of various $SiO_2/Al_2O_3$ ratios, homogenous sulfonic acids having a Hammett acidity, $H_0 < 2$, and heterogeneous sulfonic acids such as ionexchange resins. Solid phase acids containing both Bronsted and Lewis acid sites such as montmorillonite clays are also suitable for practicing the present invention.

Dialkyl ethers suitable for practicing the invention are represented by the formula R—O—R' wherein R is a primary, secondary or tertiary alkyl having from 1 to about 10 carbon atoms and R' is a primary, secondary or tertiary alkyl having from 1 to about 7 carbon atoms or a linear or branched alkoxy alkyl having from 2 to about 7 carbon atoms. Suitable carboxylic acids are represented by the formula $R''CO_2H$ wherein R" is an alkyl or aryl having from 1 to about 22 carbon atoms.

The claimed process can be carried out in a batch reactor or a continuous flow reactor under a broad range of reaction conditions including temperatures ranging from 100° to about 400° C. and pressures ranging from 1 atmosphere to about 150 atmospheres. Moreover, the process does not utilize corrosive reactants such as acid chlorides which typically require special handling and which may cause damage to the process reactor under certain conditions.

DETAILED DESCRIPTION OF THE INVENTION

The present invention is a process for producing organic esters which utilizes a new class of catalysts capable of producing a product mixture which is substantially free of water thereby overcoming problems associated with prior art processes wherein the desired organic ester must be separated from water via fractional distillation. Moreover, the present process simplifies prior art processes for producing organic esters by eliminating the necessity for tedious washing steps with basic solutions to remove residual acid catalyst from the reaction product.

Applicants' process for producing organic esters comprises reacting a carboxylic acid and a dialkyl ether in the presence of a catalyst consisting essentially of a solid phase acidic catalyst having an acidity factor of at least 0.30, preferably at least 1, under conditions sufficient to form the desired organic ester and recovering the organic ester. The reaction can be conducted at any combination of temperatures and pressures at which the reaction proceeds to form the desired organic ester. Reaction conditions suitable for practicing the present invention will vary depending upon the particular carboxylic acid and dialkyl ether utilized to form the organic ester. The process can be conducted at a temperature ranging from about 100° to about 400° C. and a pressure ranging from 1 atmosphere to about 150 atmospheres. Typically, the molar ratio of carboxylic acid to dialkyl ether ranges from 1.0:0.1 to 1:10 and preferably ranges from 1:0.5 to 1:5.

Typical reaction times vary depending on the chosen reaction conditions and the choice of reactants. However, suitable reaction times typically range from 5 minutes to 5 hours and optimum conditions can be deduced by those of ordinary skill in the art. Likewise, one of ordinary skill in the art can readily choose the carboxylic acid and dialkyl ether required to produce the organic ester to be prepared. Suitable reaction conditions can be readily determined without undue experimentation by one of organic skill in the art to which this invention pertains.

Dialkyl ethers suitable for use as reactants in the present process are represented by the formula R—O—R' wherein R is a primary, secondary or tertiary alkyl having from 1 to about 10 carbon atoms and R' is a primary, secondary or tertiary alkyl having from 1 to about 7 carbon atoms or a linear or branched alkoxy alkyl having from 2 to about 7 carbon atoms. In a preferred embodiment, the dialkyl ether is chosen such that when R is a tertiary alkyl, then R' is not a secondary of tertiary alkyl in order to reduce the amount of elimination products formed during the process.

Carboxylic acids suitable for use as reactants in the present process are represented by the formula R"$CO_2$H wherein R" is an alkyl or aryl having from 1 to about 22 carbon atoms. The term, aryl, includes unsubstituted aryls, alkyl aryls such as the tolyl group and aryl alkyls such as the benzyl group. Preferably, the carboxylic acid is a linear or branched alkyl having from 1 to about 22 carbon atoms, and most preferably, a linear alkyl having from 1 to about 10 carbon atoms. A mixture of dialkyl ethers and/or carboxylic acids can be used in the present process to produce a mixture or organic esters.

Suitable catalysts for practicing the present invention include crystalline molecular sieves which are solid phase and have an acidity factor of at least 0.30 and preferably at least 1. These highly acidic molecular sieves have sufficient catalytic activity to effect the subject reaction in high conversion. Such crystalline molecular sieves include crystalline alumino-silicates, commonly referred to as zeolites, both natural and synthetic in origin. Suitable zeolites include X, Y, K, L, faujasite, mordenite, offretite, beta, omega, gmelinite, chabazite, clinoptilolite, heulandite, dachiarite, ferrierites, brewsterite, stillbite, episbilbite and the ZSM family.

When initially prepared, the cation in the crystalline alumino-silicate usually is an alkali metal, typically sodium. This ion is desirably exchanged in sufficient proportion, generally in excess of 60%, with an acidic ion such as hydrogen; a rare earth metal including, but not limited to lanthanum, cerium, praseodymium; and transition metals including, but not limited to nickel, copper, chromium and the like for the practice of this invention. The substitution of various ions for the sodium ion alters the acidity of the zeolite thus making it more reactive and catalytically effective for the subject reaction.

The naturally occurring and synthetic zeolites normally have a silica to alumina molar ratio of from 2 to 15:1. Zeolite acidity may be altered by a technique referred to as dealumination. In effect, the practice of dealumination decreases the alumina content in the zeolite thereby increasing the silica to alumina ratio. Removal of alumina from the internal structure can also enlarge the cage structure or pore size of the zeolite thereby permitting entry and diffusion of larger molecules into its internal structure. Dealumination also tends to increase catalyst acidity.

Thus, one may be able to utilize a particular cation in a dealuminated zeolite but not use the same cation in its non-dealuminated counterpart since that catalyst would not meet the acidic requirements of this invention. Suitable techniques for dealuminating the subject zeolites include chelation, dehydration or acidification, the latter which entails treating the zeolite with an inorganic acid. These techniques are well known in the art.

Zeolites are porous materials with the pores having generally uniform molecular dimensions. Cavities or cages are formed in the zeolite and are connected by channels of generally defined diameter. Suitable cage diameters should be sufficiently large to permit molecules to effectively enter the interior of the alumino-silicate in order to react and then to exit the cavity as product. Typically the pore size will range from about 6 to 15 Angstroms but the size of the pore required can vary depending upon the product being produced. If the pore size is too small or tortuous to permit entry of the reactants, conversion will be low at low temperatures and catalytic activity will be limited to surface catalysis. Reaction temperatures may be increased to enhance molecular diffusion.

Molecular sieves have been developed which have been defined as nonzeolites but perform similarly in some reactions to zeolitic materials. These materials have a cage structure and typically contain alumina and silica in combination with other components, e.g., phosphorus, titania and the like. Representative crystalline molecular sieves are described in U.S. Pat. No. 4,440,871, European Patents 123,110 and 121,232. For purposes of this invention, these molecular sieves are deemed equivalent to and are to be included within the term molecular sieves.

Other nonalumino-silicate zeolites which can be used in the practicing the present invention include boron containing zeolites such as borosilicates and borogermanates. Bronsted acids such as amorphous silica-alumina, homogeneous sulfonic acids having a Hammett acidity, $H_0 < 2$, or heterogeneous sulfonic acids such as ion-exchange resins are preferred.

Sufficient alkali metal must be exchanged with appropriate acidic cations to render the crystalline molecular sieve acidic as defined by an acidity factor. This factor is determined by an ammonia absorption/desorption technique which involves treating the catalyst with ammonia at room temperature and then desorbing ammonia by heating to a temperature from ambient to 200° C. at 10° C./minute, then holding at 200° C. for 2 hours. The amount of ammonia irreversibly adsorbed at 200° C. is indicative of acidity and indicative of the strength of the amine/acid salt. An acidity factor of 0.30 millimoles ammonia irreversibly adsorbed per gram of catalyst at 200° C. is necessary to obtain high catalytic activity and to obtain high conversion to the subject products. The acidity factors of catalysts suitable for practicing the present invention are fully disclosed in U.S. Pat. No. 4,740,620, the specification which is incorporated by reference and made a part of this application.

Suitable solvents for practicing the present process include any solvent or mixture of solvents wherein the solvent is inert with respect to the reactants under the enumerated process conditions. The term, inert, means that the solvent will not react with the carboxylic acid or dialkyl ether under the chosen reaction conditions. Suitable solvents include hydrocarbons such as hexane, octane and the like. The choice of solvent is not critical to the practice of this invention. Those skilled in the art will recognize that the reactants and/or organic ester product may serve as a reaction medium in certain cases thereby eliminating the necessity of introducing an inert solvent.

The process of the present invention can be operated either in a batch mode in the liquid phase or as a continuous process. When operated in a continuous mode, the reactor is operated at a LHSV ranging from 0.1 to about 10. In carrying out the present invention on a commercial scale, the process is preferably operated in a continuous mode wherein the desired organic ester is removed continuously from the reactor. Suitable reactors can be constructed of any suitable corrosion-resistant material.

In a preferred embodiment of the present invention, methyl acetate can be formed by reacting dimethyl ether and acetic acid in the presence of a catalyst consisting essentially of a solid phase acid having an acidity factor of at least 0.30, preferably at least 1, under conditions sufficient to form methyl acetate and recovering the methyl acetate from the reaction mixture. Suitable reaction conditions range from room temperature to about 220° C. when homogeneous Bronsted or Lewis acids are employed and from 50° to about 450° C. when heterogeneous Bronsted or Lewis acids are employed. The process for producing methyl acetate is typically carried out at pressures between atmospheric and 1800 psi, preferably, between atmospheric to 1000 psi. Consistent with the general embodiment of this invention, the process for producing methyl acetate can be carried oat in a batch reactor or a continuous flow reactor.

Typically, the molar ratio of acetic acid to dimethyl ether ranges from 1:0.1 to 1:10 and preferably, between 1:0.5 and 1:5.

The following examples are given to illustrate the process of the present invention and should not be construed as limiting the scope.

EXPERIMENTAL SECTION

Runs 1-25 illustrate the pr of the present invention wherein a dialkyl ether and a carboxylic acid are reacted in the presence of a solid phase acid catalyst having an acidity of greater than about 0.30. The Runs presented in the Examples were conducted in a 1.0 cm. I.D. down flow, fixed-bed reactor containing a 5 cc Vicor preheat bed in front of a 25 cc catalyst bed. The reactor was constructed with 304 stainless steel and was jacketed with a single-element heater. The reactor was flooded with dimethyl ether (DME) at 25° C. at a pressure of 700-800 psig. After establishing the desired DME flow rate and the initial reactor temperature, the desired acetic acid flow rate was established. Samples were isolated in a −78° C. trap over a period of 1.5 hours, and the total mass balances (in and out of the reactor) were obtained.

Mass balances for these examples were all in the range of 85% to 106% with product accountability greater than 98%. The alkylation products and acetic acid were analyzed by the same DB-1701 FSOT capillary column interface to a flame ionization detector. The structures of all organic compounds were verified by GC/MS. The lower limit of detection for the components of interest was approximately 0.002 wt. %

EXAMPLE 1

Reaction of Acetic Acid and Dimethyl Ether over γ-Alumina Catalyst

Acetic acid and dimethyl ether (molar ratio 1:2) were reacted in the presence of a γ-alumina catalyst in the form of ⅛ inch extrudates at 325° C. and a pressure of 829 psig. γ-Alumina is primarily a Lewis type, heterogeneous acid catalyst. With a HOAc to DME molar ratio of 1:2 and an LHSV of 0.19, 92.03% of the acetic acid was converted to methyl acetate with a methanol to methyl acetate product ratio of 0.32.

EXAMPLE 2-6

Reaction of Acetic Acid and Dimethyl Ether Over κ-Alumina Catalyst

Examples 2-6, set forth in Table 2, summarize data obtained by reacting acetic acid and dimethyl ether over κ-alumina in the form of 12/18 mesh granules under a variety of reaction conditions. The κ-alumina catalyst was obtained from Alcoa, Inc., Pittsburgh, Pa., and is primarily a Lewis type, heterogeneous acid catalyst having an acid strength of greater than 0.4. Runs 2 through 6 demonstrate that conversion of acetic acid to methyl acetate is strongly affected by temperature. Run 6, conducted at a temperature of 325° C., provided about 75% conversion of acetic acid to methyl acetate. However, the amount of methanol produced during the reaction also increases as the reaction temperature is increased.

TABLE 2

| Run | Temp. (°C.) | Pres. (psig) | LHSV Molar | HOAc:DME Feed | % HOAc Conv. | MeOH:MeOAc Product Ratio |
|---|---|---|---|---|---|---|
| 2 | 200 | 704 | 0.33 | 1:4 | 0.28 | 0.00 |

TABLE 2-continued

| Run | Temp. (°C.) | Pres. (psig) | LHSV Molar | HOAc:DME Feed | % HOAc Conv. | MeOH:MeOAc Product Ratio |
|---|---|---|---|---|---|---|
| 3 | 250 | 702 | 0.33 | 1:4 | 9.28 | 0.01 |
| 4 | 275 | 722 | 0.33 | 1:4 | 23.66 | 0.02 |
| 5 | 300 | 721 | 0.33 | 1:4 | 34.39 | 0.07 |
| 6 | 325 | 714 | 0.33 | 1:4 | 74.43 | 0.31 |

EXAMPLE 7-12

Reaction of Acetic Acid and Dimethyl Ether Over a Silica-Alumina Catalyst

Examples 7-12, set forth in Table 3, summarize data obtained by reacting acetic acid and dimethyl ether over a silica/alumina catalyst comprising 13% alumina and 87% silica in the form of 12/18 mesh granules under a variety of reaction conditions. The catalyst, an amorphous mixture of alumina and silica, was obtained from Davison Specially Chemical Co., Baltimore, Md., and demonstrates primarily Bronsted type acidity. The catalyst had much more acid strength than the Lewis acid catalysts described in Examples 1-6. The data demonstrate that conversion of acetic acid to methyl acetate increases with increasing temperature although greater amounts of methanol are produced with increasing temperature.

TABLE 3

| Run | Temp. (°C.) | Pres. (psig) | LHSV Molar | HOAc:DME Feed | % HOAc Conv. | MeOH:MeOAc Product Ratio |
|---|---|---|---|---|---|---|
| 7 | 200 | 846 | 0.19 | 1:2 | 84.68 | 0.13 |
| 8 | 225 | 758 | 0.19 | 1:2 | 86.33 | 0.16 |
| 9 | 175 | 790 | 0.19 | 1:2 | 92.11 | 0.22 |
| 10 | 150 | 804 | 0.19 | 1:2 | 45.33 | 0.04 |
| 11 | 175 | 741 | 0.19 | 1:2 | 12.20 | 0.01 |
| 12 | 125 | 746 | 0.19 | 1:2 | 7.42 | 0.01 |

EXAMPLES 13-23

Reaction of Acetic Acid and Dimethyl Ether Over a Montmorilonite Catalyst

Examples 13-25, set forth in Table 4, summarize data obtained by reacting acetic acid and dimethyl ether over Montinorillonite K-10 clay, in the form of 12/18 mesh granules, under a variety of reaction conditions. The catalyst, obtained from United Catalysts, Inc., Louisville, Ky., demonstrates both Lewis and Bronsted type acidity. Again, the data demonstrate that exceptionally high conversion of acetic acid to methyl acetate and selectivity to the desired product can be obtained using the solid acid catalysts of the present invention.

TABLE 4

| Run | Temp. (°C.) | Pres. (psig) | LHSV Molar | HOAc:DME Feed | % HOAc Conv. | MeOH:MeOAc Product Ratio |
|---|---|---|---|---|---|---|
| 13 | 150 | 784 | 0.19 | 1:2 | 90.51 | 0.24 |
| 14 | 175 | 791 | 0.19 | 1:2 | 88.43 | 0.25 |
| 15 | 200 | 800 | 0.19 | 1:2 | 90.48 | 0.25 |
| 16 | 175 | 801 | 0.26 | 1:3 | 90.48 | 0.27 |
| 17 | 150 | 780 | 0.26 | 1:3 | 92.43 | 0.26 |
| 18 | 150 | 790 | 0.26 | 1:3 | 93.88 | 0.27 |
| 19 | 150 | 783 | 0.26 | 1:3 | 98.39 | 0.26 |
| 20 | 125 | 720 | 0.26 | 1:3 | 17.60 | 0.03 |
| 21 | 125 | 720 | 0.26 | 1:5 | 18.83 | 0.02 |
| 22 | 150 | 781 | 0.26 | 1:5 | 94.55 | 0.32 |
| 23 | 150 | 781 | 0.26 | 1:5 | 94.25 | 0.32 |
| 24 | 150 | 790 | 0.26 | 1:3 | 90.87 | 0.29 |
| 25 | 150 | 782 | 0.26 | 1:3 | 91.27 | 0.27 |

The present invention offers numerous advantages over conventional processes for producing organic esters. For example, while typical processes produce an azeotropic mixture of the desired organic ester and water, the claimed process utilizes a combination of reactants and catalysts wherein water is not produced in appreciable amounts. Therefore, the organic ester product can be separated conveniently thereby avoiding a cumbersome azeotropic distillation step as required in prior art processes.

The catalysts of the present invention, some of which are heterogeneous in form, provide a substantial benefit over homogeneous catalysts in that the desired product formed using a heterogeneous catalyst can be isolated by separating the catalyst from the reaction mixture by simple filtration. In contrast, product isolation from a homogeneously catalyzed reaction requires catalyst neutralization and aqueous workup.

While the embodiments of process of the present process have been disclosed with reference to specific examples, one of ordinary skill can make various changes and modifications to the invention to adapt it to various uses and conditions. As such, these changes and modifications are properly, equitably, and intended to be, within the full range of equivalents of the following claims.

Having thus described the present invention, what is now deemed appropriate for Letters Patent is set forth in the following claims.

We claim:

1. A process for producing an organic ester comprising reacting a carboxylic acid and a dialkyl ether in the presence of a catalyst consisting essentially of a solid phase Lewis acid catalyst selected from the group consisting of gamma-alumina and κ-alumina having an acidity factor of at least 0.30, under conditions sufficient to form the ester and recovering the ester.

2. The process according to claim 1 wherein the reaction is conducted at a temperature ranging from 100° to about 400° C. and a pressure ranging from 1 atmosphere to about 150 atmospheres.

3. The process according to claim 2 wherein the dialkyl ether is represented by the formula R—O—R' wherein R is a primary, secondary or tertiary alkyl having from I to about 10 carbon atoms and R' is a primary, secondary or tertiary alkyl having from 1 to about 7 carbon atoms or a linear or branched alkoxy alkyl having from 2 to about 7 carbon atoms.

4. The process according to claim 3 wherein the carboxylic acid is represented by the formula R"CO$_2$H wherein R" is an alkyl or aryl having from 1 to about 22 carbon atoms.

5. The process according to claim 4 wherein the reaction is carried out in a batch reactor or a continuous flow reactor.

6. The process according to claim 1 wherein the carboxylic acid is acetic acid and the dialkyl ether is dimethyl ether.

7. A process for producing an organic ester comprising reacting a carboxylic acid and a dialkyl ether in the presence of a catalyst consisting essentially of a a solid phase Lewis acid catalyst selected from the group consisting of gamma-alumina and κ-alumina having an acidity factor of greater than 1, under conditions sufficient to form the organic ester and recovering the organic ester.

8. The process according to claim 7 wherein the dialkyl ether is represented by the formula R—O—R' wherein R is a primary, secondary or tertiary alkyl having from 1 to about 10 carbon atoms and R' is a primary, secondary or tertiary alkyl having from 1 to about 7 carbn atoms or a linear or branched alkoxy alkyl having from 2 to about 7 carbon atoms with the proviso that when R is a tertiary alkyl then R' is not a secondary or tertiary alkyl.

9. The process according to claim 7 wherein the carboxylic acid is represented by the formula R"CO$_2$H wherein R" is an linear or branched alkyl, having from 1 to about 22 carbon atoms.

10. The process according to claim 7 wherein the reaction is conducted at a temperature ranging from 100° to about 400° C. and a pressure ranging from 1 atmosphere to about 150 atmospheres.

11. The process according to claim 10 wherein the dialkyl ether is represented by the formula R—O—R' wherein R is a primary, secondary or tertiary alkyl having from 1 to about 10 carbon atoms and R' is a primary, secondary or tertiary alkyl having from 1 to about 7 carbon atoms or a linear or branched alkoxy alkyl having from 2 to about 7 carbon atoms.

12. The process according to claim 10 wherein the carboxylic acid is represented by the formula R"CO$_2$H wherein R" is an alkyl or aryl having from 1 to about 22 carbon atoms.

* * * * *

UNITED STATES PATENT AND TRADEMARK OFFICE
CERTIFICATE OF CORRECTION

PATENT NO. : 5,298,650

DATED : March 29, 1994

INVENTOR(S) : Waller et al.

It is certified that error appears in the above-identified patent and that said Letters Patent is hereby corrected as shown below:

<u>In the Claims:</u>

Column 10, line 8, delete "carbn" and insert -- carbon --.

Signed and Sealed this

Fifth Day of July, 1994

*Attest:*

BRUCE LEHMAN

*Attesting Officer*     *Commissioner of Patents and Trademarks*